(12) United States Patent
Sawa

(10) Patent No.: US 7,829,544 B2
(45) Date of Patent: Nov. 9, 2010

(54) AQUEOUS SOLUTION PREPARATION CONTAINING AMINOGLYCOSIDE ANTIBIOTIC AND BROMFENAC

(75) Inventor: Shirou Sawa, Kobe (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 10/578,359

(22) PCT Filed: Nov. 12, 2004

(86) PCT No.: PCT/JP2004/016849

§ 371 (c)(1),
(2), (4) Date: Jun. 6, 2006

(87) PCT Pub. No.: WO2005/046700

PCT Pub. Date: May 26, 2005

(65) Prior Publication Data

US 2007/0082857 A1    Apr. 12, 2007

(30) Foreign Application Priority Data

Nov. 14, 2003  (JP) ................ 2003-384646

(51) Int. Cl.
*A01N 43/04* (2006.01)
*A61K 31/70* (2006.01)

(52) U.S. Cl. ........................................ 514/40
(58) Field of Classification Search ........................ None
See application file for complete search history.

(56) References Cited

U.S. PATENT DOCUMENTS

| 4,910,225 A | 3/1990 | Ogawa et al. |
| 5,414,011 A | 5/1995 | Fu et al. |
| 6,060,486 A | 5/2000 | Urashima et al. |
| 6,281,224 B1 | 8/2001 | Miyagi et al. |
| 6,440,964 B1 * | 8/2002 | Cagle et al. ............ 514/230.5 |

FOREIGN PATENT DOCUMENTS

| EP | 0 336 200 | 10/1989 |
| EP | 0 711 546 | 5/1996 |
| JP | 2-124817 | 5/1990 |
| JP | 2-286627 | 11/1990 |
| JP | 8-291065 | 11/1996 |
| JP | 9-301866 | 11/1997 |
| JP | 2000-212088 | 8/2000 |
| WO | 94/17785 | 8/1994 |
| WO | 95/33457 | 12/1995 |
| WO | 02/30395 | 4/2002 |

OTHER PUBLICATIONS

H. Guo et al., "Ion-Paired Codrug for Increased Ocular Absorption", Proceed. Int'l. Symp. Control Release Bioact. Mater, vol. 24, pp. 617-618; 1997.

* cited by examiner

*Primary Examiner*—Shaojia Anna Jiang
*Assistant Examiner*—Layla Bland
(74) *Attorney, Agent, or Firm*—Wenderoth, Lind & Ponack, L.L.P.

(57) ABSTRACT

Stable and clear aqueous solution preparations comprising an aminoglycoside antibiotic or a pharmacologically acceptable salt thereof and bromfenac being a nonsteroidal antiinflammatory agent or a pharmacologically acceptable salt thereof.

8 Claims, No Drawings

AQUEOUS SOLUTION PREPARATION CONTAINING AMINOGLYCOSIDE ANTIBIOTIC AND BROMFENAC

This application is a U.S. national stage of International Application No. PCT/JP2004/016849 filed Nov. 12, 2004.

TECHNICAL FIELD

The present invention relates to an aqueous solution preparation comprising an aminoglycoside antibiotic or its pharmacologically acceptable salt and a non-steroidal antiinflammatory bromfenac or its pharmacologically acceptable salt.

BACKGROUND ART

Aminoglycoside antibiotics have a broad antibacterial spectrum against gram-positive and gram-negative bacteria, and it is said that their action mechanism is based on inhibition of bacterial protein synthesis. Since even after blood concentration of the aminoglycoside antibiotics is decreased to a concentration of MIC (minimum inhibitory concentration) or less, and the aminoglycoside antibiotics exhibit post-antibiotic effect (PAE) on the inhibition of bacterial growth, it is known that the aminoglycoside antibiotics show long-lasting inhibitory effect on the inhibition of bacterial growth even after a short period of contact with gram-positive and gram-negative bacteria. For this reason, various aminoglycoside antibiotics such as gentamicin, tobramycin, streptomycin, amikacin, arbekacin, and the like have been widely used via systemic administration of oral preparations, injections, or the like, or via topical administration of eye drops, nose drops, ear drops or the like for the treatment of infectious diseases caused by *Pseudomonas, Proteus, Escherichia coli* or *Staphylococcus* such as hematosepsis, bronchitis, pneumonia, pyelitis, cystitis, peritonitis, blepharitis, hordeolum, conjunctivitis, keratitis, dacryocystitis, tympanititis, external otitis, parasinusitis, and the like.

As mentioned above, aminoglycoside antibiotics are effective against infectious diseases. It is, however, important to simultaneously suppress inflammations associated with infection in infectious diseases. It is known that combination use of antibiotics with anti-inflammatory agents can ameliorate quickly infectious site of inflammations. With respect to aqueous solution preparations, a combination drug of an aminoglycoside antibiotic with a steroidal anti-inflammatory agent, for example, a combination drug of fradiomycin sulfate with betamethasone sodium phosphate has been practically used in the form of an aqueous solution preparation in the field of ophthalmology and otorhinolaryngology.

However, there is a problem that said combination drugs cause adverse effects which are known in steroid preparations, such as induction of infection, exacerbation of infectious diseases, secondary hypocorticosteroidism, glaucoma, posterior subcapsular cataract, and the like. For this reason, a combination solution preparation of an aminoglycoside antibiotic with a non-steroidal antiinflammatory agent, having no side effects as mentioned above, is considered to be very useful. However, for example, when tobramycin is combined with diclofenac sodium which is a non-steroidal antiinflammatory agent, there is a problem that precipitation or suspension formation occurs (see Non-patent literature: Ion-paired codrug for increased ocular absorption, Proceed. Int'Symp. Control. Rel. Bioact. Mater., 24 (1997)), making it difficult to prepare an aqueous solution preparation comprising an aminoglycoside antibiotic and a nonsteroidal anti-inflammatory agent.

Bromfenac is a non-steroidal antiinflammatory agent represented by the formula (I):

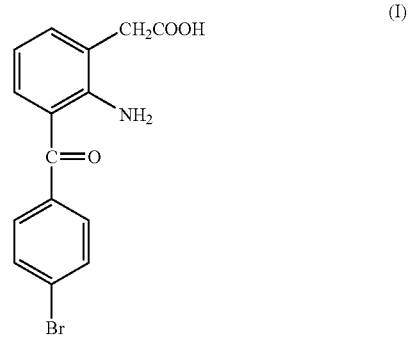

and its chemical name is 2-amino-3-(4-bromobenzoyl)phenylacetic acid. Bromfenac is effective against inflammatory diseases (e.g. blepharitis, conjunctivis, scleritis, postoperative inflammation) of the extraocular segment or the anterior ocular segment in the field of ophthalmology, and in particular, its efficacy for treating uveitis is equal to nonsteroidal antiinflammatory agents which have previously been used (see Patent literature 1: Japanese patent no. 2683676 corresponding to U.S. Pat. No. 4,910,225). Bromfenac has been practically used as its sodium salt in the form of eye drops in the field of ophthalmology.

However, with respect to a combined aqueous solution preparation comprising bromfenac and an aminoglycoside antibiotic, stable combined preparations have not yet been known, due to the difficulty in formulation of the above aminoglycoside antibiotic with the non-steroidal antiinflammatory agent.

DISCLOSURE OF THE INVENTION

Problem to be Solved by the Invention

It is an object of the present invention to provide a stable and clear aqueous solution preparation containing an aminoglycoside antibiotic or its pharmacologically acceptable salt and bromfenac or its pharmacologically acceptable salt.

Means for Solving the Problem

The inventors of the present invention have intensively studied on the above problems, resulting in finding that an aqueous solution preparation containing an aminoglycoside antibiotic and bromfenac does not cause precipitation by adjusting the pH to 7.0 or higher, which was an unexpected finding. However, it was found that precipitation occurred gradually when such aqueous solution was preserved. Then, the inventors of the present invention have further studied on a method causing no precipitation even after preservation. As a result, they have found that a stable aqueous solution wherein no precipitation occurred was provided by further adding citric acid or its pharmacologically acceptable salt, monoethanolamine or its pharmacologically acceptable salt, N-methylglucamine or its pharmacologically acceptable salt, nicotinamide, a nonionic water-soluble polymer or a nonionic surfactant to the above aqueous solution. The present invention has been completed based on these findings.

That is, the present invention relates to the followings.

(1) An aqueous solution preparation comprising an aminoglycoside antibiotic or its pharmacologically acceptable salt and bromfenac or its pharmacologically acceptable salt.

(2) The aqueous solution preparation according to the above (1), further comprising at least one compound selected from the group consisting of citric acid or its pharmacologically acceptable salt, monoethanolamine or its pharmacologically acceptable salt, N-methylglucamine or its pharmacologically acceptable salt, and nicotinamide.

(3) The aqueous solution preparation according to the above (2), wherein the pH of said preparation is within a range of 7.0 to 8.5.

(4) The aqueous solution preparation according to the above (1), further comprising at least one compound selected from the group consisting of a nonionic water-soluble polymer and a nonionic surfactant.

(5) The aqueous solution preparation according to the above (4), wherein the pH of said preparation is within a range of 6.0 to 8.5.

(6) The aqueous solution preparation according to any one of the above (1) to (5), wherein the aminoglycoside antibiotic is tobramycin or gentamicin.

(7) The aqueous solution preparation according to any one of the above (1) to (5), wherein the concentration of the aminoglycoside antibiotic or its pharmacologically acceptable salt in the aqueous solution preparation is within a range from a minimum of 0.01 w/v % to a maximum of 35.0 w/v %, and the concentration of the bromfenac or its pharmacologically acceptable salt in the aqueous solution preparation is within a range from a minimum of 0.01 w/v % to a maximum of 0.5 w/v %.

(8) The aqueous solution preparation according to any one of the above (1) to (7), which is an eye drop, a nose drop, an ear drop or an injection.

EFFECT OF THE INVENTION

A stable and clear aqueous solution preparation comprising an aminoglycoside antibiotic or its pharmacologically salt and bromfenac or its pharmacologically salt can be provided by the present invention.

Accordingly, the aqueous solution preparation of the present invention can be used as an eye drop for the treatment of, for example, blepharitis, hordeolum, conjunctivitis, keratitis, dacryocystitis, etc., as a nose drop for the treatment of, for example, acute rhinitis, acute paranasal sinusitis, sinusitis (empyema), etc., as an ear drop for the treatment of, for example, external auditory canal cholesteatoma, acute external otitis, perichondritis, phlegmon of external auditory meatus, auricular celluritis, malignant otitis externa, necrotic otitis externa, otitis externa caused by *Pseudomonas aeruginosa*, otitis externa diffusa, other infectious otitis externa, or acute otitis media, or as an injection for the treatment of various infectious diseases.

BEST MODE FOR CARRYING OUT THE INVENTION

The aminoglycoside antibiotics used in the aqueous solution preparation of the present invention includes tobramycin, astromycin, amikacin, arbekacin, isepamicin, kanamycin, gentamicin, sisomicin, dibekacin, streptomycin, netilmicin, paromomycin, fradiomycin, bekanamycin, micronomicin, ribostamycin, and the like.

The pharmacologically acceptable salt of the aminoglycoside antibiotics includes an inorganic salt (e.g. hydrochloride, sulfate, etc.) and an organic salt (e.g. acetate, etc.).

Among the aminoglycoside antibiotics or pharmacologically acceptable salts thereof, especially preferred are tobramycin, gentamicin, and gentamicin sulfate.

Bromfenac used in the aqueous solution preparation of the present invention can be prepared, for example, by the method described in Journal of Medicinal Chemistry, vol. 27, pp. 1370-1388 (1984) or U.S. Pat. No. 1,136,375, or according to the method described therein.

As the pharmacologically acceptable salt of bromfenac, there are exemplified the alkali metal salts (e.g. sodium salt, potassium salt, etc.) and the alkaline earth metal salts (e.g. calcium salt, magnesium salt, etc.). Among these salts, the sodium salt is especially preferable. Furthermore, bromfenac or its pharmacologically acceptable salt may be obtained in the form of hydrates, depending on synthetic conditions and recrystallization conditions. These hydrates may be used in the aqueous solution preparation of the present invention. Such hydrates include, for example, 3/2 hydrate.

The aqueous solution preparation of the present invention contains preferably citric acid or its pharmacologically acceptable salt, monoethanolamine or its pharmacologically acceptable salt, N-methylglucamine or its pharmacologically acceptable salt, or nicotin amide. These compounds may be used alone or in combination thereof.

The pharmacologically acceptable salt of citric acid used in the aqueous solution preparation of the present invention includes the alkali metal salts (e.g. sodium salt, potassium salt, etc.), the alkaline earth metal salts (e.g. calcium salt, magnesium salt, etc.), the ammonium salt, and the like. Further, citric acid or its pharmacologically acceptable salt may be a hydrate. Examples of citric acid or its pharmacologically acceptable salt include, for example, citric anhydride, citric acid monohydrate, monopotassium citrate, anhydrous tripotassium citrate, tripotassium citrate monohydrate, calcium citrate tetrahydrate, sodium citrate, disodium citrate, anhydrous trisodium citrate, trisodium citrate dihydrate, anhydrous sodium dihydrogen citrate, magnesium citrate nonahydrate, ammonium citrate, triammonium citrate, ammonium dihydrogen citrate, and the like.

The pharmacologically acceptable salt of monoethanolamine or N-methylglucamine used in the aqueous solution preparation of the present invention includes inorganic salts (e.g. hydrochloride, sulfate, etc.), organic salts (e.g. acetate, etc.), and the like.

Citric acid or its pharmacologically acceptable salt, monoethanolamine or its pharmacologically acceptable salt, N-methylglucamine or its pharmacologically acceptable salt, or nicotinamide may be used alone or in combination thereof.

Further, the aqueous solution preparation of the present invention may preferably contain a nonionic water-soluble polymer or a nonionic surfactant. The nonionic water-soluble polymer includes, for example, polyvinyl alcohol, polyvinylmethyl ether, polyvinylpyrrolidone (e.g. povidone K-30, etc.), methylcellulose, ethylcellulose, hydroxymethyl cellulose, hydroxyethyl cellulose, hydroxypropyl cellulose, hydroxypropylmethyl cellulose, α-cyclodextrin, and the like. Preferable examples of the nonionic water-soluble polymer are polyvinylpyrrolidone, polyvinyl alcohol or α-cyclodextrin.

The nonionic surfactant includes, for example, polyoxyethylene sorbitan fatty acid esters (e.g. polysorbate 20, polysorbate 60, polysorbate 80, etc.); tyloxapol; polyoxyl 40 monostearate; polyoxyethylene hydrogenated castor oil (e.g. polyoxyethylene (40) hydrogenated castor oil, polyoxyethylene (60) hydrogenated castor oil, etc.); poloxamer; and the like. Preferable examples of the nonionic surfactant are polysorbate 80, tyloxapol or polyoxyl 40 monostearate.

The nonionic water-soluble polymer or nonionic surfactant mentioned above may be used alone or in combination thereof.

In addition, the nonionic water-soluble polymer or nonionic surfactant mentioned above may be used in combination with the above citric acid or its pharmacologically acceptable salt, monoethanolamine or its pharmacologically acceptable salt, N-methylglucamine or its pharmacologically acceptable salt, or nicotinamide. Preferable examples of such combination can be, for example, citric acid or its pharmacologically acceptable salt and a nonionic water-soluble polymer (e.g. povidone K-30, polyvinyl alcohol, α-cyclodextrin, etc.); citric acid or its pharmacologically acceptable salt and a nonionic surfactant (e.g. tyloxapol, polysorbate 80, polyoxyl 40 monostearate, etc.); monoethanolamine or its pharmacologically acceptable salt and a nonionic water-soluble polymer (e.g. povidone K-30, polyvinyl alcohol, α-cyclodextrin, etc.); monoethanolamine or its pharmacologically acceptable salt and a nonionic surfactant (e.g. tyloxapol, polysorbate 80, polyoxyl 40 monostearate, etc.); N-methylglucamine or its pharmacologically acceptable salt and a nonionic water-soluble polymer (e.g. povidone K-30, polyvinyl alcohol, α-cyclodextrin, etc.); N-methylglucamine or its pharmacologically acceptable salt and a nonionic surfactant (e.g. tyloxapol, polysorbate 80; polyoxyl 40 monostearate, etc.); nicotinamide and a nonionic water-soluble polymer (e.g. povidone K-30, polyvinyl alcohol, α-cyclodextrin, etc.); nicotinamide and a nonionic surfactant (e.g. tyloxapol, polysorbate 80, polyoxyl 40 monostearate, etc.); a nonionic surfactant (e.g. tyloxapol, polysorbate 80, polyoxyl 40 monostearate, etc.) and a nonionic water-soluble polymer (e.g. povidone K-30, polyvinyl alcohol, α-cyclodextrin, etc.), or the like.

The aqueous solution preparation of the present invention is preferably adjusted to an arbitrary pH with a pH adjustment agent. As the pH adjustment agent, it is possible to use any pH adjustment agent so long as it is a conventional one used in the production of pharmaceutical preparations. Examples of such pH adjustment agents are acids or bases, including, for example, hydrochloric acid, sodium hydroxide, potassium hydroxide, sodium carbonate, phosphoric acid, and acetic acid. With respect to the pH of the aqueous solution preparation of the present invention, for example, the aqueous solution preparation comprising an aminoglycoside antibiotic or its pharmacologically acceptable salt and bromfenac or its pharmacologically acceptable salt is preferably adjusted to a pH of about not less than 7.0, usually within a pH range of about 7.0 to about 8.5. It is preferable to adjust the pH within a range of about 7.0 to about 8.5 even in the case where citric acid or its pharmacologically acceptable salt, monoethanolamine or its pharmacologically acceptable salt, N-methylglucamine or its pharmacologically acceptable salt, or nicotinamide is further added to the aqueous solution preparation comprising the aminoglycoside antibiotic or its pharmacologically acceptable salt and bromfenac or its pharmacologically acceptable salt. In addition, a stable aqueous solution preparation can be prepared in a pH range of about 6.0 to about 7.0, usually about 6.0 to about 8.5, in the case where a nonionic water-soluble polymer or a nonionic surfactant is further added to the aqueous solution preparation comprising the aminoglycoside antibiotic or its pharmacologically acceptable salt and bromfenac or its pharmacologically acceptable salt. The most preferable pH range of the aqueous solution preparation of the present invention is about 7.5 to 8.5.

There is no particular limitation on the amount of the pH adjustment agent, and such pH adjustment agent to be added may be used alone or in combination.

Although the concentration of the principal ingredient aminoglycoside antibiotic in the aqueous solution preparation of the present invention varies depending on the kind of aminoglycoside antibiotics to be used, and there is no particular limitation thereon, it is appropriately selected usually from a range of minimum concentration of about 0.01 w/v %, preferably about 0.1 w/v %, to maximum concentration of about 35.0 w/v %, preferably about 10.0 w/v %. For example, in the case of tobramycin, its concentration is usually within a range of minimum concentration of about 0.01 w/v %, preferably about 0.1 w/v %, to maximum concentration of about 5.0 w/v %, preferably about 1.0 w/v %. The especially preferable concentration of tobramycin is about 0.3 to 0.5 w/v %. In the case of gentamicin sulfate, its concentration is usually within a range of minimum concentration of about 0.01 w/v %, preferably about 0.1 w/v %, to maximum concentration of about 10.0 w/v %, preferably about 5.0 w/v %. The especially preferable concentration of gentamicin sulfate is about 0.3 to 0.5 w/v %.

It is preferable to appropriately vary the concentration of the aminoglycoside antibiotic, depending on the purpose of use and the degree of disease conditions to be applied.

Although there is no particular limitation on the concentration of bromfenac which is another principal ingredient, or its pharmacologically acceptable salt, in the aqueous solution preparation of the present invention, it is usually within a range of minimum concentration of about 0.01 w/v %, preferably about 0.05 w/v %, to maximum concentration of about 0.5 w/v %, preferably about 0.2 w/v %. Especially preferred concentration is about 0.1 to 0.2 w/v %.

It is preferable to appropriately vary the concentration of bromfenac, depending on the purpose of use and the degree of disease conditions to be applied.

Although there is no particular limitation on the concentration of citric acid or its pharmacologically acceptable salt used in the aqueous solution preparation of the present invention, it is usually within a range of minimum concentration of about 0.01 w/v %, preferably about 0.05 w/v %, to maximum concentration of about 5.0 w/v %, preferably about 0.3 w/v %.

Although there is also no particular limitation on the concentration of monoethanolamine or its pharmacologically acceptable salt, N-methylglucamine or its pharmacologically acceptable salt, or nicotinamide used in the aqueous solution preparation of the present invention, it is usually within a range of minimum concentration of about 0.01 w/v %, preferably about 0.05 w/v %, to maximum concentration of about 5.0 w/v %, preferably about 1.0 w/v %. Furthermore, there is no particular limitation on the concentration of the nonionic water-soluble polymer or nonionic surfactant in the aqueous solution preparation of the present invention, but it is within a range of minimum concentration of about 0.01 w/v %, preferably about 0.05 w/v %, to maximum concentration of about 10.0 w/v %, preferably about 1.0 w/v %.

The aqueous solution preparation of the present invention can be appropriately used in the form of eye drops, nose drops, ear drops or injections.

The aqueous solution preparation of the present invention can be prepared by the per se known method or according to the method as described in the Japanese Pharmacopoeia, 14$^{th}$ Edition, General Rules for Preparations, Liquids and Solutions or Ophthalmic Solutions.

For example, in the production of eye drops, an additive commonly used in eye drops is dissolved in a solvent (e.g. purified water or water for injections), and to this solution were added an aminoglycoside antibiotic (e.g. gentamicin sulfate, etc.) and bromfenac sodium. The mixture was dissolved and adjusted to a pH of about not less than 7.0, preferably to a pH of about 7.5 to about 8.5, using a pH adjustment agent.

Alternatively, citric acid or its pharmacologically acceptable salt, monoethanolamine or its pharmacologically acceptable salt, nicotinamide, or N-methylglucamine or its pharmacologically acceptable salt, and an additive usually used in eye drops may be added to the above solvent, thereby to prepare a solution. To the solution were added an aminoglycoside antibiotic (e.g. tobramycin, gentamicin sulfate, etc.) and bromfenac sodium, and the resulting solution was adjusted to a pH of about not less than 7.0, preferably 7.5 to 8.5.

In addition, a nonionic water-soluble polymer or a nonionic surfactant and an additive commonly used in dye drops may be added to and dissolved in the solvent mentioned above, thereby to prepare a solution. To the solution were added an aminoglycoside antibiotic (e.g. tobramycin, gentamicin sulfate, etc.) and bromfenac sodium, and the resulting solution was adjusted to a pH of about not less than 6.0, preferably 7.5 to 8.5.

Examples of the additives used in the above eye drops include, for example, isotonic agents (e.g. sodium chloride, potassium chloride, glycerine, mannitol, sorbitol, boric acid, glucose, propylene glycol, etc.), buffers (e.g. phosphate buffer, acetate buffer, borate buffer, carbonate buffer, citrate buffer, Tris buffer, glutamic acid, $\epsilon$-aminocaproic acid, etc.), preservatives (e.g. benzalkonium chloride, benzetonium chloride, chlorhexidine gluconate, chlorobutanol, benzyl alcohol, sodium dehydroacetate, p-oxybenzoic acid esters, sodium edetate, boric acid, etc.). Although the amount of these additives varies depending on their kind and use, they may be added and used at any concentration so long as the purpose of the present invention is achieved.

In the production of nose drops, ear drops or injections, a conventional additive used in the above eye drops may be used.

Examples of the additives used commonly in the injections are, for example, stabilizers (e.g. sodium edetate, thioglycolic acid, etc.), soothing agents (e.g. benzyl alcohol, etc.), isotonics (e.g. sodium chloride, glycerine, concentrated glycerine, mannitol, etc.), buffers (e.g. sodium citrate, citric acid, sodium acetate, sodium hydrogen phosphate, etc.) or preservatives (e.g. chlorobutanol, etc.).

Another same or different kind of pharmaceutical ingredients may be appropriately added to the aqueous solution preparation of the present invention so long as they do not contradict the purpose of the present invention.

The aqueous solution preparation of the present invention can be applied to warm-blooded animals such as human, rat, mouse, rabbit, cow, pig, dog, cat, and the like.

The aqueous solution preparation of the present invention can be used as an eye drop for the treatment of, for example, blepharitis, hordeolum, conjunctivitis, keratitis, dacryocystitis, etc. The dose in the case where an eye drop comprising 0.1 w/v % bromfenac sodium hydrate and 0.3 w/v % tobramycin or 0.3 w/v % gentamicin sulfate is applied may be 1 to 2 drops per single administration and three to six times per day. Depending on the degree of disease conditions, administration frequency will be appropriately varied.

In the case where the aqueous solution preparation of the present invention comprising, for example, 0.1 w/v % bromfenac sodium hydrate and 0.3 w/v % tobramycin or 0.3 w/v % gentamicin sulfate is applied in the form of a nose drop for the treatment of, for example, acute rhinitis, acute paranasal sinusitis, sinusitis (empyema), etc., the dosage may be 1 to 3 drops per single administration and 3 to 6 drops per day.

In the case where the aqueous solution preparation of the present invention comprising, for example, 0.1 w/v % bromfenac sodium hydrate and 0.3 w/v % tobramycin or 0.3 w/v % gentamicin sulfate is applied in the form of an ear drop for the treatment of, for example, external auditory canal cholesteatoma, acute otitis externa, auricular perichondritis, external auditory meatus celluritis, auricular celluritis, malignant otitis externa, necrotic otitis externa, otitis externa caused by *Pseudomonas aeruginosa*, otitis externa diffusa, other infectious otitis externa, or acute otitis media, the dosage may be 1 to 2 drops per single administration and 3 to 6 drops per day.

For the treatment of various infectious diseases by the aqueous solution preparation of the present invention, an injection comprising, for example, 0.1 w/v % bromfenac sodium hydrate and 0.3 w/v % tobramycin or 0.3 w/v % gentamicin sulfate may be applied intramuscularly or subcutaneously in an appropriate amount.

The present invention will be illustrated in more detail by way of the following Examples, but it is to be construed that the present invention is not limited by these Examples.

Examples 1

Test-1 of the Change in Formulation

The formulations as shown in Table 1 were prepared. The formulation 1 was prepared by dissolving boric acid and borax in a fixed amount of purified water and adding tobramycin and bromfenac sodium to the solution, followed by dissolution. With respect to the formulation 2, sodium citrate was further added to the formulation 1, and then purified water was added thereto to a prescribed amount. The formulation 3 was prepared by dissolving boric acid and borax in a fixed amount of purified water and adding gentamicin sulfate and bromfenac sodium thereto to make a solution. Then, the pH values of these formulations were adjusted by addition of hydrochloric acid and sodium hydroxide. Appearances of these formulations were observed with the naked eye.

The appearance was determined based on the following criteria.

Clear: the solution is transparent

Turbid: the solution is yellowish cloudy when viewed on a black background

Slightly turbid: the degree of the turbidity in the solution is lower compared to that of the above "turbid" criterion Suspended: fine particles are floating in the solution, and the solution is yellowish cloudy when viewed on a black background Strongly turbid: fine particles are floating in the solution to such an extent that the background is not visible, or precipitates are formed.

TABLE 1

| Composition | Formulation of combination solution (w/v %) | | |
|---|---|---|---|
| | Formulation 1 | Formulation 2 | Formulation 3 |
| Bromfenac sodium | 0.1 | 0.1 | 0.1 |
| Tobramycin | 0.3 | 0.3 | — |

TABLE 1-continued

| | Formulation of combination solution (w/v %) | | |
|---|---|---|---|
| Composition | Formulation 1 | Formulation 2 | Formulation 3 |
| Gentamicin sulfate | — | — | 0.3 |
| Boric acid | 1.1 | 1.1 | 0.57 |
| Borax | 1.1 | 1.1 | 2.25 |
| Sodium citrate | — | 0.3 | — |
| Hydrochloric acid | q.s | q.s | q.s |
| Sodium hydroxide | q.s. | q.s. | q.s. |
| Purified water | q.s. | q.s. | q.s. |

The results of the Test on change in formulation were shown in Table 2.

TABLE 2

| Formulation 1 | | Formulation 2 | | Formulation 3 | |
|---|---|---|---|---|---|
| pH | Appearance | pH | Appearance | pH | Appearance |
| 7.83 | Yellow clear | 7.46 | Yellow clear | 7.35 | Yellow clear |
| 7.61 | Yellow clear | 7.12 | Yellow clear | 7.08 | Yellow clear |
| 7.27 | Slightly turbid | 6.59 | Suspended | 6.96 | Slightly turbid |
| 7.16 | Turbid | | | 6.79 | Turbid |
| 6.66 | Suspended | | | 6.49 | Suspended |

As apparent from Table 2, it was found that turbidity and suspension formation occurred with the decrease of the pH. That is, when the pH is within a range of less than 6.6, precipitation occurred in any one of the formulations 1, 2, and 3. A yellow clear solution preparation was obtained in the formulation 1 by adjusting the pH to not less than 7.5. In the formulation 2 wherein 0.3 w/v % sodium citrate was added, a yellow clear solution preparation was also obtained by adjusting the pH to not less than 7.1. In the case of the formulation 3, there was obtained a yellow clear solution preparation by adjusting the pH to not less than 7.1.

Example 2

Test-2 of the Change in Formulation

A combination solution comprising tobramycin and bromfenac sodium as shown in Table 3 was prepared (formulation 4). Boric acid and borax were added to and dissolved in a fixed amount of purified water, and to this solution were added tobramycin and bromfenac sodium, followed by dissolution. Separately, each additive was added to and dissolved in the prescribed amount of purified water to give an additive solution (shown in Table 4). The above combination solution and the additive solution were mixed in a ratio of 1:1, and the mixture was adjusted to a pH of 7.0 by addition of hydrochloric acid. The appearance of each sample solution was observed with the naked eye. The appearance was determined according to the criteria as described in Example 1.

TABLE 3

| Formulation of combination solution | |
|---|---|
| Component | Formulation 4 w/v % |
| Bromfenac sodium | 0.2 |
| Tobramycin | 0.6 |
| Boric acid | 1.14 |
| Borax | 4.5 |
| Hydrochloric acid | q.s. |
| Sodium hydroxide | q.s. |
| Purified water | q.s. |

TABLE 4

| Concentration of each additive in additive solutions | |
|---|---|
| Additive | w/v % |
| No additive (purified water) | 0 |
| Monoethanolamine | 2.0 |
| N-Methylglucamine | 2.0 |
| Nicotinamide | 2.0 |
| Dipotassium glycyrrhizinate | 0.2 |
| Potassium sorbate | 0.4 |
| Sodium glutamate | 0.6 |
| N-Methyl-2-pyrrolidone | 2.0 |
| Povidone K-30 | 4.0 |
| Sodium alginate | 0.2 |
| Sodium chondroitin sulfate | 2.0 |
| Polysorbate 80 | 0.6 |
| Tyloxapol | 0.6 |
| Polyoxyl 40 monostearate | 0.6 |
| Benzalkonium chloride | 0.2 |
| Sodium lauryl sulfate | 0.2 |

The test results of the appearance of the combination solutions containing an additive are shown in Table 5.

TABLE 5

| Additive | Final concentration | Appearance |
|---|---|---|
| Control (no additive) | — | turbid |
| Monoethanolamine | 1.0 w/v % | clear |
| N-Methylglucamine | 1.0 w/v % | slightly turbid |
| Nicotinamide | 1.0 w/v % | clear |
| Dipotassium glycyrrhizinate | 0.1 w/v % | strongly turbid |
| Potassium sorbate | 0.2 w/v % | turbid |
| Sodium glutamate | 0.3 w/v % | turbid |
| N-Methyl-2-pyrrolidone | 1.0 w/v % | turbid |
| Povidone K-30 | 2.0 w/v % | clear |
| Sodium alginate | 0.1 w/v % | strongly turbid |
| Sodium chondroitin sulfate | 1.0 w/v % | strongly turbid |
| Polysorbate 80 | 0.3 w/v % | clear |
| Tyloxapol | 0.3 w/v % | clear |
| Polyoxyl 40 monostearate | 0.3 w/v % | clear |
| Benzalkonium chloride | 0.1 w/v % | strongly turbid |
| Sodium lauryl sulfate | 0.1 w/v % | strongly turbid |

The above Table 5 indicates that the appearance is preferable in the order of "clear", "slightly turbid" and "turbid" for the aqueous solution preparations of the present invention. However, the preparation with "strongly turbid" is not preferred for the aqueous solution preparation of the present invention. As apparent from Table 5, turbidity occurrence in the preparations was inhibited or reduced by adding an organic amine such as monoethanolamine and N-methylglucamine; nicotinamide; a nonionic water-soluble polymer such as povidone K-30; or a nonionic surfactant such as polysorbate 80, tyloxapol, and polyoxyl 40 monostearate.

Example 3

Test-3 of the Change in Formulation

Combination solutions comprising gentamicin sulfate and bromfenac sodium as shown in Table 6 were prepared (formulations 5 and 6). The formulation 5 was prepared by adding sodium dihydrogen phosphate and concentrated glycerine to a fixed amount of purified water, dissolving the mixture, and adding gentamicin sulfate and bromfenac sodium thereto, followed by dissolution. With respect to the formulation 6, boric acid and borax was added to and dissolved in a fixed amount of purified water, and to this solution were added gentamicin sulfate and bromfenac sodium, and then the mixture was dissolved. Separately, each additive solution was prepared as shown in Table 7. Each additive was added to and dissolved in a prescribed amount of water. The above combination solution and the additive solution were mixed in a ratio of 1:1. Polyvinyl alcohol and α-cyclodextrin were respectively admixed with the formulation 5, and other additives were each admixed with the formulation 6. The resulting solutions were each adjusted to a pH of 6.5 by the addition of hydrochloric acid. The solution with addition of polysorbate 80 and α-cyclodextrin was also adjusted to a pH of 6.0. The appearances of the mixed solutions thus prepared were observed with the naked eye. The appearance was determined according to the criteria as described in Example 1.

TABLE 6

| Component | Formulation of combination solution (w/v %) | |
| --- | --- | --- |
| | Formulation 5 | Formulation 6 |
| Bromfenac sodium | 0.2 | 0.2 |
| Gentamicin sulfate | 0.6 | 0.6 |
| Boric acid | — | 1.14 |
| Borax | — | 4.5 |
| Sodium dihydrogen phosphate | 0.2 | — |
| Concentrated glycerine | 5.2 | — |
| Hydrochloric acid | q.s. | q.s. |
| Sodium hydroxide | q.s. | q.s. |
| Purified water | q.s. | q.s. |

TABLE 7

| Concentration of each additive in additive solutions | |
| --- | --- |
| Additive | w/v % |
| No additive (Purified water) | 0 |
| Sodium citrate | 0.2 |
| Monoethanolamine | 2.0 |
| N-Methylglucamine | 2.0 |
| Nicotinamide | 2.0 |
| Potassium sorbate | 0.4 |
| Povidone K-30 | 4.0 |
| Polyvinyl alcohol | 2.0 |
| α-Cyclodextrin | 4.0 |
| Sodium alginate | 0.2 |
| Polysorbate 80 | 0.6 |
| Tyloxapol | 0.6 |
| Polyoxyl 40 monostearate | 0.6 |

TABLE 7-continued

| Concentration of each additive in additive solutions | |
| --- | --- |
| Additive | w/v % |
| Benzalkonium chloride | 0.2 |
| Sodium lauryl sulfate | 0.2 |

The appearance of the solutions in the Test of the change in formulations was shown in Table 8 in terms of additives.

TABLE 8

| Additive | | | | |
| --- | --- | --- | --- | --- |
| Component | Final concentration (w/v %) | Combination formulation | pH | Appearance |
| Control (No additive) | — | Formulation 6 | 6.5 | Suspended |
| Sodium citrate | 0.1 | Formulation 6 | 6.5 | Clear |
| Monoethanolamine | 1.0 | Formulation 6 | 6.5 | clear |
| N-Methylglucamine | 1.0 | Formulation 6 | 6.5 | Slightly turbid |
| Nicotinamide | 1.0 | Formulation 6 | 6.5 | Clear |
| Potassium sorbate | 0.2 | Formulation 6 | 6.5 | Suspended |
| Povidone K-30 | 2.0 | Formulation 6 | 6.5 | Clear |
| Polyvinyl alcohol | 1.0 | Formulation 5 | 6.5 | Clear |
| α-Cyclodextrin | 2.0 | Formulation 5 | 6.5 | Clear |
| α-Cyclodextrin | 2.0 | Formulation 5 | 6.0 | Clear |
| Sodium alginate | 0.1 | Formulation 6 | 6.5 | Strongly turbid |
| Polysorbate 80 | 0.3 | Formulation 6 | 6.5 | Clear |
| Polysorbate 80 | 0.3 | Formulation 6 | 6.0 | Clear |
| Tyloxapol | 0.3 | Formulation 6 | 6.5 | Clear |
| Polyoxyl 40 monostearate | 0.3 | Formulation 6 | 6.5 | Clear |
| Benzalkonium chloride | 0.1 | Formulation 6 | 6.5 | Strongly turbid |
| Sodium lauryl sulfate | 0.1 | Formulation 6 | 6.5 | Strongly turbid |

In the above Table 8, the appearances of the solutions are preferable in the order of "clear", "slightly turbid", and "turbid" for the aqueous solution preparation of the present invention. The preparation with "suspended" or "strongly turbid" is not preferred for the aqueous solution preparation of the present invention. As clearly seen from Table 8, turbidity occurrence in the preparations are inhibited or reduced by adding sodium citrate; an organic amine such as monoethanolamine and N-methylglucamine; nicotinamide; a nonionic water-soluble polymer such as povidone, polyvinyl alcohol, and α-cyclodextrin; or a nonionic surfactant such as polysorbate 80, tyloxapol, and polyoxyl 40 monostearate. Furthermore, when α-cyclodextrin as a nonionic water-soluble polymer, or polysorbate 80 as a nonionic surfactant was added, precipitation formation was inhibited even at a pH of 6.0.

Formulation Example 1

Eye Drop

TABLE 9

| Bromfenac sodium 3/2 hydrate | 0.1 | g |
| --- | --- | --- |
| Tobramycin | 0.3 | g |
| Boric acid | 1.4 | g |
| Borax | 0.8 | g |
| Hydrochloric acid | q.s. | |
| Purified water | q.s. | |
| Total volume | 100 | ml |
| pH | 7.8 | |

Borax was dissolved in about 80 ml of purified water. Tobramycin and bromfenac sodium were added to the solution, and the mixture was dissolved. To the solution was added boric acid, and the mixture was dissolved. The pH of the solution was adjusted with hydrochloric acid, and purified water was added thereto to make a total volume of 100 ml.

Formulation Example 2

Ear Drop

TABLE 10

| | |
|---|---|
| Bromfenac sodium 3/2 hydrate | 0.1 g |
| Tobramycin | 0.3 g |
| Boric acid | 1.8 g |
| Sodium citrate | 0.3 g |
| Sodium hydroxide | q.s. |
| Purified water | q.s. |
| Total volume | 100 ml |
| pH | 8.0 |

Tobramycin and bromfenac sodium were added to and dissolved in about 80 ml of purified water. To the solution were added sodium citrate and boric acid, and the mixture was dissolved. The pH of the solution was adjusted with sodium hydroxide, and purified water was added thereto to make a total volume of 100 ml.

Formulation Example 3

Nose Drop

TABLE 11

| | |
|---|---|
| Bromfenac sodium 3/2 hydrate | 0.1 g |
| Gentamicin sulfate | 0.3 g |
| Polysorbate 80 | 0.3 g |
| Sodium dihydrogen phosphate | 0.1 g |
| Concentrated glycerine | 2.6 g |
| Sodium hydroxide | q.s. |
| Purified water | q.s. |
| Total volume | 100 ml |
| pH | 7.5 |

Sodium dihydrogen phosphate, concentrated glycerine and polysorbate 80 were added to and dissolved in about 80 ml of purified water. To the solution were added gentamicin sulfate and bromfenac sodium, and the mixture was dissolved. Sodium hydroxide was added to the solution to adjust the pH, and purified water was added thereto to make a total volume of 100 ml.

Formulation Example 4

Eye Drop

TABLE 12

| | |
|---|---|
| Bromfenac sodium 3/2 hydrate | 0.1 g |
| Tobramycin | 0.3 g |
| Boric acid | 1.6 g |
| Povidone K-30 | 2.0 g |
| Sodium hydroxide | q.s. |
| Purified water | q.s. |
| Total volume | 100 ml |
| pH | 7.8 |

Tobramycin and bromfenac sodium were added to and dissolved in about 80 ml of purified water. To the solution were added povidone K-30 and boric acid, and the mixture was dissolved. The pH of the solution was adjusted with sodium hydroxide, and purified water was added thereto to make a total volume of 100 ml.

Formulation Example 5

Eye Drop

TABLE 13

| | |
|---|---|
| Bromfenac sodium 3/2 hydrate | 0.1 g |
| Tobramycin | 0.3 g |
| Boric acid | 1.6 g |
| N-Methylglucamine | 1.0 g |
| Sodium hydroxide | q.s. |
| Purified water | q.s. |
| Total volume | 100 ml |
| pH | 7.8 |

Tobramycin and bromfenac sodium were added to and dissolved in about 80 ml of purified water. To the solution were added N-methylglucamine and boric acid, and the mixture was dissolved. The pH of the solution was adjusted with sodium hydroxide, and purified water was added to make a total volume of 100 ml.

Formulation Example 6

Eye Drop

TABLE 14

| | |
|---|---|
| Bromfenac sodium 3/2 hydrate | 0.1 g |
| Tobramycin | 0.3 g |
| Boric acid | 1.6 g |
| Borax | 0.6 g |
| Povidone K-30 | 1.0 g |
| N-Methylglucamine | 0.1 g |
| Sodium hydroxide | q.s. |
| Purified water | q.s. |
| Total volume | 100 ml |
| pH | 7.8 |

Tobramycin and bromfenac sodium were added to and dissolved in about 80 ml of purified water. To the solution were added povidone K-30, N-methylglucamine, boric acid and borax, and the mixture was dissolved. The pH of the solution was adjusted with sodium hydroxide, and purified water was added thereto to make a total volume of 100 ml.

Formulation Example 7

Eye Drop

TABLE 15

| | |
|---|---|
| Bromfenac sodium 3/2 hydrate | 0.1 g |
| Tobramycin | 0.3 g |
| Boric acid | 1.6 g |
| Borax | 0.7 g |

TABLE 15-continued

| | |
|---|---|
| Benzalkonium chloride | 0.005 g |
| Tyloxapol | 0.02 g |
| Povidone K-30 | 1.0 g |
| Sodium edetate | 0.02 g |
| Sodium hydroxide | q.s. |
| Purified water | q.s. |
| Total volume | 100 ml |
| pH | 8.0 |

Tobramycin and bromfenac sodium were added to and dissolved in about 80 ml of purified water. To the solution were added tyloxapol, povidone K-30, sodium edetate, benzalkonium chloride, boric acid and borax, and the mixture was dissolved. The pH of the solution was adjusted with sodium hydroxide, and purified water was added thereto to make a total volume of 100 ml.

INDUSTRIAL APPLICABILITY

In accordance with the present invention, it is possible to obtain a clear aqueous solution preparation comprising an aminoglycoside antibiotic or its pharmacologically acceptable salt and bromfenac sodium or its pharmacologically acceptable salt.

Accordingly, the aqueous solution preparation of the present invention can be used, for example, as an eye drop for the treatment of blepharitis, hordeolum, conjunctivitis, keratitis, dacryocystitis, etc., or as a nose drop for the treatment of, for example, acute rhinitis, acute paranasal sinusitis, sinusitis (empyema), etc., as an ear drop for the treatment of, for example, cholesteatoma of external auditory canal, acute external otitis, auricular perichondritis, phlegmon of external auditory meatus, auricular celluritis, malignant otitis externa, necrotic otitis externa, otitis externa caused by *Pseudomonas aeruginosa*, otitis externa diffusa, other infectious otitis externa, or acute otitis media, or as an injection for the treatment of various infectious diseases.

The invention claimed is:

1. An aqueous solution preparation comprising (a) an aminoglycoside antibiotic or its pharmacologically acceptable salt, (b) bromfenac or its pharmacologically acceptable salt and (c) nicotinamide.

2. The aqueous solution preparation according to claim 1, wherein the pH of said preparation is within a range of 7.0 to 8.5.

3. The aqueous solution preparation according to claim 1, further comprising (d) at least one compound selected from the group consisting of a nonionic water-soluble polymer and a nonionic surfactant.

4. The aqueous solution preparation according to claim 1, wherein the aminoglycoside antibiotic is tobramycin or gentamicin.

5. The aqueous solution preparation according to claim 1, wherein the concentration of the aminoglycoside antibiotic or its pharmacologically acceptable salt in the aqueous solution preparation is within a range from a minimum of 0.01 w/v % to a maximum of 35.0 w/v %, and the concentration of the bromfenac or its pharmacologically acceptable salt in the aqueous solution preparation is within a range from a minimum of 0.01 w/v % to a maximum of 0.5 w/v %.

6. The aqueous solution preparation according to claim 1, which is an eye drop, a nose drop, an ear drop or an injection.

7. The aqueous solution preparation according to claim 3, wherein the nonionic water-soluble polymer is polyvinylpyrrolidone, polyvinyl alcohol or α-cyclodextrin, and the nonionic surfactant is polysorbate 80, tyloxapol or polyoxyl 40 monostearate.

8. A method for preventing occurrence of precipitation in an aqueous solution preparation comprising an aminoglycoside antibiotic or its pharmacologically acceptable salt and bromfenac or its pharmacologically acceptable salt, which comprises adding nicotinamide to the aqueous solution preparation comprising an aminoglycoside antibiotic or its pharmacologically acceptable salt and bromfenac or its pharmacologically acceptable salt.

* * * * *